US008712733B2

(12) United States Patent
Beaudry et al.

(10) Patent No.: US 8,712,733 B2
(45) Date of Patent: Apr. 29, 2014

(54) ADJUSTING DENTAL PROSTHESES BASED ON SOFT TISSUE

(75) Inventors: Jean-Sebastien Auclair Beaudry, Quebec (CA); David Giasson, Quebec (CA)

(73) Assignee: Biocad Medical, Inc., Quebec (CA)

( * ) Notice: Subject to any disclaimer, the term of this patent is extended or adjusted under 35 U.S.C. 154(b) by 464 days.

(21) Appl. No.: 12/885,027

(22) Filed: Sep. 17, 2010

(65) Prior Publication Data

US 2012/0072178 A1 Mar. 22, 2012

(51) Int. Cl.
| G06F 17/50 | (2006.01) |
| G06F 19/00 | (2011.01) |
| A61C 3/00 | (2006.01) |
| A61C 13/00 | (2006.01) |
| A61C 13/225 | (2006.01) |
| A61C 5/00 | (2006.01) |
| A61C 5/08 | (2006.01) |

(52) U.S. Cl.
USPC ...... 703/1; 700/98; 433/21; 433/24; 433/167; 433/183; 433/215; 433/218; 433/219

(58) Field of Classification Search
None
See application file for complete search history.

(56) References Cited

U.S. PATENT DOCUMENTS

| 5,273,429 | A | | 12/1993 | Nappi et al. | |
| 5,674,069 | A | | 10/1997 | Osorio | |
| 6,049,743 | A | * | 4/2000 | Baba | 700/163 |
| 6,217,334 | B1 | | 4/2001 | Hultgren | |
| 6,231,342 | B1 | | 5/2001 | Osorio et al. | |
| 7,134,874 | B2 | | 11/2006 | Chishti et al. | |
| 7,140,877 | B2 | | 11/2006 | Kaza | |
| 7,228,191 | B2 | | 6/2007 | Hofmeister et al. | |
| 7,245,753 | B2 | * | 7/2007 | Squilla et al. | 382/128 |
| 7,471,821 | B2 | * | 12/2008 | Rubbert et al. | 382/154 |
| 7,762,814 | B2 | | 7/2010 | Van der Zel | |
| 2001/0021498 | A1 | | 9/2001 | Osorio et al. | |
| 2002/0110786 | A1 | | 8/2002 | Dillier | |
| 2003/0039389 | A1 | * | 2/2003 | Jones et al. | 382/154 |
| 2004/0081938 | A1 | * | 4/2004 | Chishti et al. | 433/24 |
| 2004/0185422 | A1 | | 9/2004 | Orth et al. | |
| 2004/0220691 | A1 | * | 11/2004 | Hofmeister et al. | 700/98 |
| 2004/0265770 | A1 | * | 12/2004 | Chapoulaud et al. | 433/24 |
| 2005/0186540 | A1 | * | 8/2005 | Taub et al. | 433/223 |
| 2006/0008776 | A1 | | 1/2006 | Orth et al. | |
| 2006/0063135 | A1 | * | 3/2006 | Mehl | 433/223 |
| 2006/0105294 | A1 | | 5/2006 | Burger et al. | |
| 2006/0115793 | A1 | * | 6/2006 | Kopelman et al. | 433/215 |
| 2006/0122719 | A1 | * | 6/2006 | Kopelman et al. | 700/98 |
| 2006/0204078 | A1 | * | 9/2006 | Orth et al. | 382/154 |
| 2006/0275737 | A1 | * | 12/2006 | Kopelman et al. | 433/213 |
| 2007/0233299 | A1 | * | 10/2007 | Kopelman et al. | 700/98 |

(Continued)

FOREIGN PATENT DOCUMENTS

| CA | 2519979 | 9/2005 |
| WO | WO 2009/070469 | 6/2009 |

*Primary Examiner* — Omar Fernandez Rivas
*Assistant Examiner* — Nithya J Moll
(74) *Attorney, Agent, or Firm* — Knobbe, Martens, Olson & Bear, LLP.

(57) ABSTRACT

Herein are provided methods, systems, computer-readable media, techniques and processes for adjusting dental prostheses based on soft tissue. These include allowing an operator to define the surface of a dental prosthesis, such as an abutment, that is proximal to the patient's gum relative to a 3D scan of the patient's gums. The operator can define the offset of that surface as well as the limits of that surface.

20 Claims, 13 Drawing Sheets

(56) References Cited

U.S. PATENT DOCUMENTS

| | | | |
|---|---|---|---|
| 2007/0292821 A1* | 12/2007 | De Vreese | 433/195 |
| 2008/0015727 A1 | 1/2008 | Dunne et al. | |
| 2009/0047629 A1* | 2/2009 | Kim | 433/173 |
| 2009/0248184 A1* | 10/2009 | Steingart et al. | 700/98 |
| 2009/0325128 A1* | 12/2009 | Holzner et al. | 433/201.1 |
| 2011/0224955 A1* | 9/2011 | Fisker et al. | 703/1 |

* cited by examiner

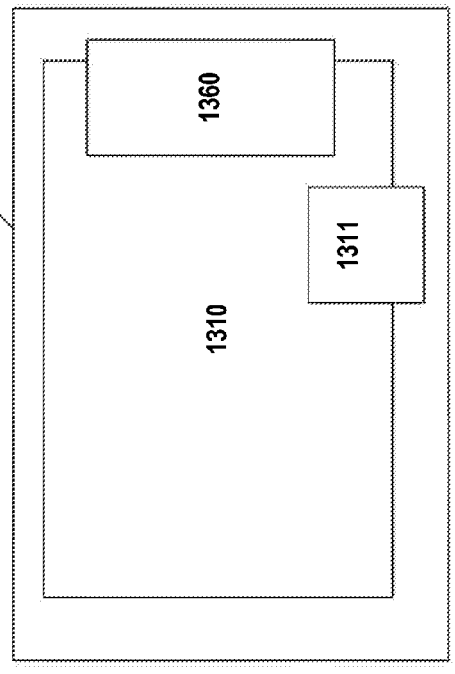
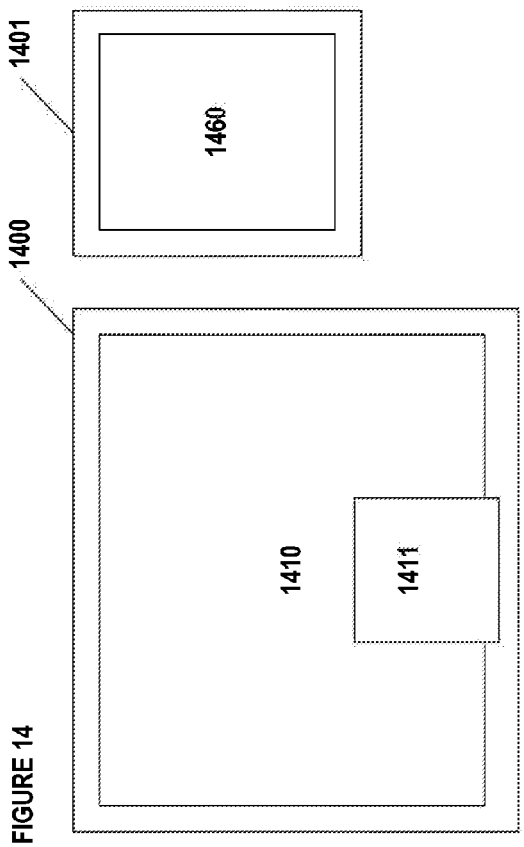

ADJUSTING DENTAL PROSTHESES BASED ON SOFT TISSUE

BACKGROUND

1. Field

The present application generally relates to dental planning, and more particularly to adjusting dental prostheses based on soft tissue.

2. Description of Related Technology

The use of computer systems to design dental prostheses has increased in recent years. The computer systems allow a dentist, dental technician, or other operator to design dental prostheses for individual patients. These individual prosthesis designs are often called "situations," "dental plans," or "prosthetic plans." Operators using the computer systems can design plans based on a library of the teeth shapes and positions, patient data, and available equipment and hardware.

In prior systems, abutment shapes were manipulated by hand. In these systems, an operator might be given access to a 3D scan of the soft tissue in the area where an abutment would be placed. The operator could manipulate individual "handles" on the 3D model in order to move the 3D surface of the abutment relative to the soft tissue (e.g., to match the soft tissue's 3D surface). But manipulating the 3D surface of the abutment can be time consuming and difficult. The operator would have to manipulate multiple individual points on the 3D surface of the abutment in order to attempt to form it to the desired shape. The techniques, methods, systems, and computer-readable media herein provide solutions to some of these problems.

SUMMARY

Presented herein are techniques, methods, systems, devices, and computer-readable media for adjusting dental prostheses based on soft tissue. This summary in no way limits the invention herein, but instead is provided to summarize a few of the embodiments.

Embodiments herein include techniques, methods, systems, devices, and computer-readable media for adjusting dental prostheses based on soft tissue, including receiving a 3D scan of soft tissue of the patient. The 3D scan of the soft tissue of the patient can include an emergence portion. The emergence portion of the 3D scan of the soft tissue may extend from an area associated with an implant attached to said patient, to an area where a dental prosthesis attached to said implant would emerge from said soft tissue. Emergence limit information for an emergence surface of a 3D model of the dental prosthesis may be received. Desired offset information for the emergence surface of the 3D model of the dental prosthesis may be received. The offset information comprises a distance between the emergence surface of the 3D model of the dental prosthesis and the emergence portion of the 3D scan of the soft tissue. A shape of the emergence surface of the 3D model of the dental prosthesis may be determined based on the emergence portion of the 3D scan of the soft tissue, the emergence limit information, and the offset information. Further, manufacturing data related to the dental prosthesis may be produced.

Numerous other embodiments are described throughout herein.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

FIG. 13 illustrates a tenth interface for adjusting dental prostheses based on soft tissue.

FIG. 14 illustrates an eleventh interface for adjusting dental prostheses based on soft tissue.

DETAILED DESCRIPTION OF SPECIFIC EMBODIMENTS

Overview

In various embodiments herein, an operator, such as a dentist, dental surgeon, or the like, can define the portion ("the emergence portion") of a prosthesis', such as an abutment's, surface that runs from the implant, through the soft tissue ("the emergence surface"), to the base of the prosthesis. The emergence portion of the prosthesis' surface may be roughly matched to the soft tissue's surface by defining a desired offset from the soft tissue and effectuating the offset by, for example, pressing a button or performing a keystroke. The operator may first perform a 3D scan of the soft tissue around the area in which the abutment will be placed. In some cases, the 3D scan of the soft tissue may come from another lab or another operator. Regardless of the origin of the 3D scan of the soft tissue surface, the operator can use the 3D scan of the soft tissue as a guide for creating the abutment. The operator can define an offset to make the abutment's 3D emergence surface larger than, smaller than, or equal to (zero offset) the 3D scan of the soft tissue. Once the operator presses the button, the 3D emergence surface of the abutment is modified automatically to be offset from the 3D scan of the soft tissue by the desired amount. Embodiments herein may be used to design any type of prosthesis that may emerge through soft tissue.

An operator might want to design a dental prosthesis so that, once it is installed in the patient's mouth, it will compress the surrounding soft tissue, thereby leaving no gap between the dental prosthesis and the soft tissue. In other cases, the operator may want to match the dental prosthesis with the soft tissue, thereby reducing both the gap between the soft tissue in the dental prosthesis as well as the compression of the soft tissue. In some cases, the operator may want to leave a gap between the dental prosthesis and the soft tissue. Embodiments herein will allow the operator to design dental prosthesis s in any of these ways.

Figure 1:
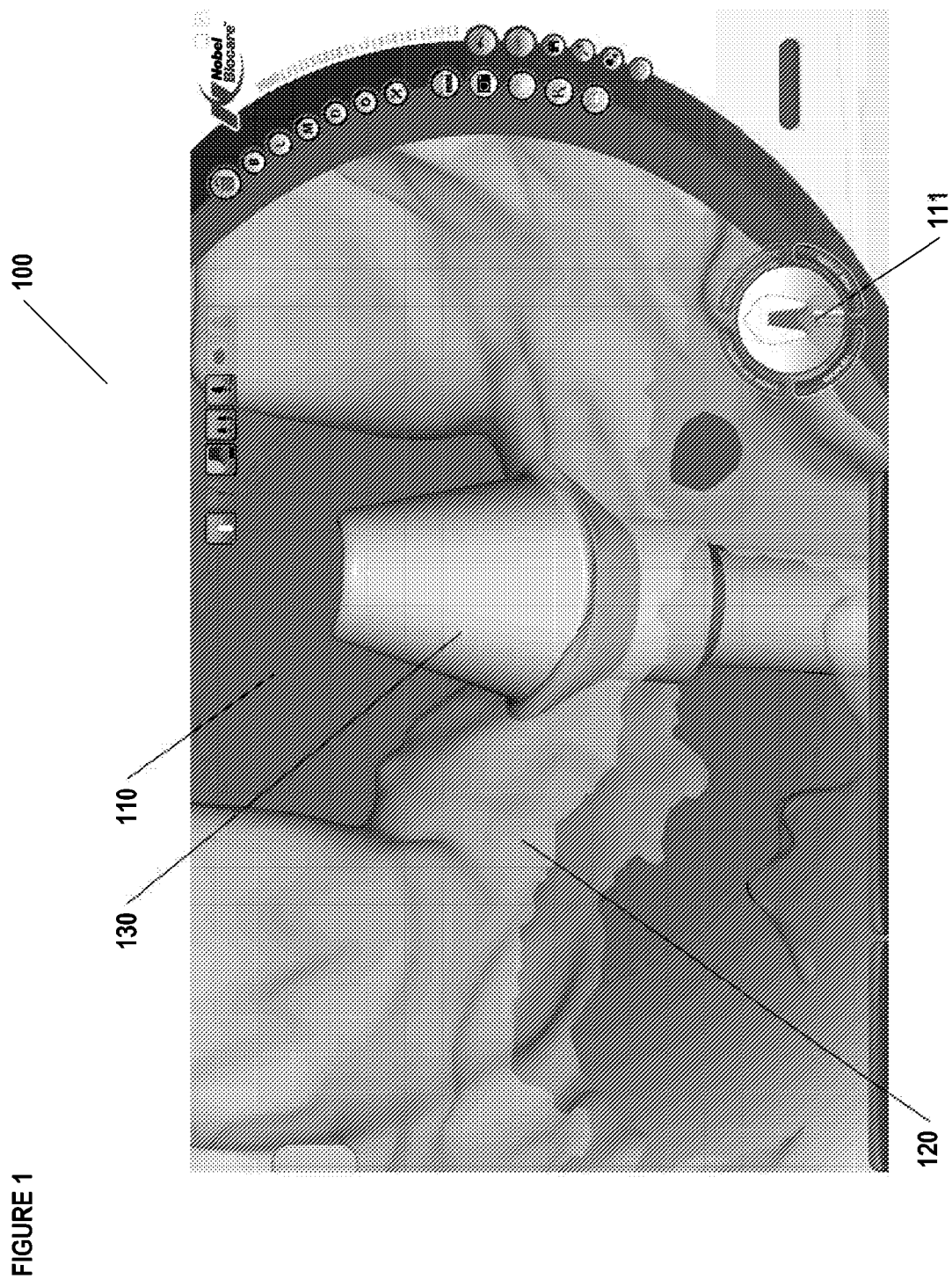
FIG. 1 illustrates a first interface for adjusting dental prostheses based on soft tissue.

FIG. 1 depicts an interface 100 that has a global abstraction portion 111, an overlaid representation portion 110, and depicts the 3D scan of soft tissue 120, as well as an abutment 130. In some embodiments, the operator can use the global abstraction portion 111 to selectively turn on and off the viewing of certain items that will be displayed in overlaid representation portion 110. For example, the operator may be able to turn on or off the viewing of a prosthesis such as abutment 130, the soft tissue 120, and/or any other item that may be displayed in the overlaid representation portion 110. Examples and embodiments of selection techniques are given in U.S. patent application Ser. No. 12/703,601, filed Feb. 10, 2010, entitled Dental Prosthetics Manipulation, Selection, and Planning, which is hereby incorporated by reference in its entirety for all purposes.

Figure 4:
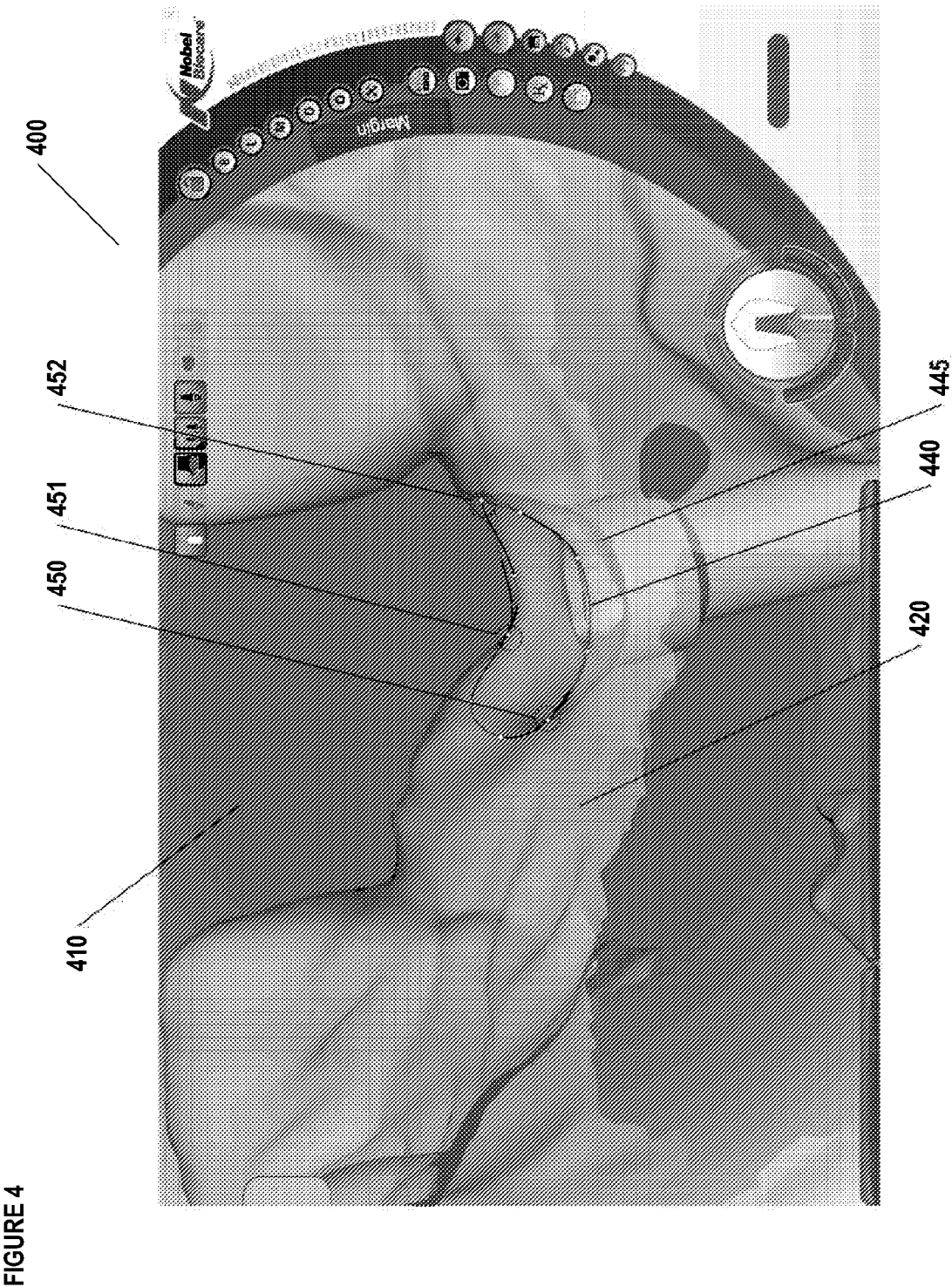
FIG. 4 illustrates a second interface for adjusting dental prostheses based on soft tissue.

The operator can use the interface 100 to manipulate the shape of the surface of the abutment 130. FIG. 4 depicts an interface 400 including an overlaid representation portion 410. An operator can define an emergence limit 440 for a dental prosthesis (not pictured) with respect to the 3D scan of soft tissue 420. The 3D scan of the soft tissue has an "emergence portion." The phrase "emergence portion of the 3D scan of the soft tissue" has its ordinary and customary meaning, which includes signifying at least a surface or a portion of a surface that extends from an emergence limit down toward a scanned implant. For example, an emergence portion of 3D scan 420 extends from an emergence limit 440 down to the implant, which is signaled as 445 in FIG. 4.

Figure 5:
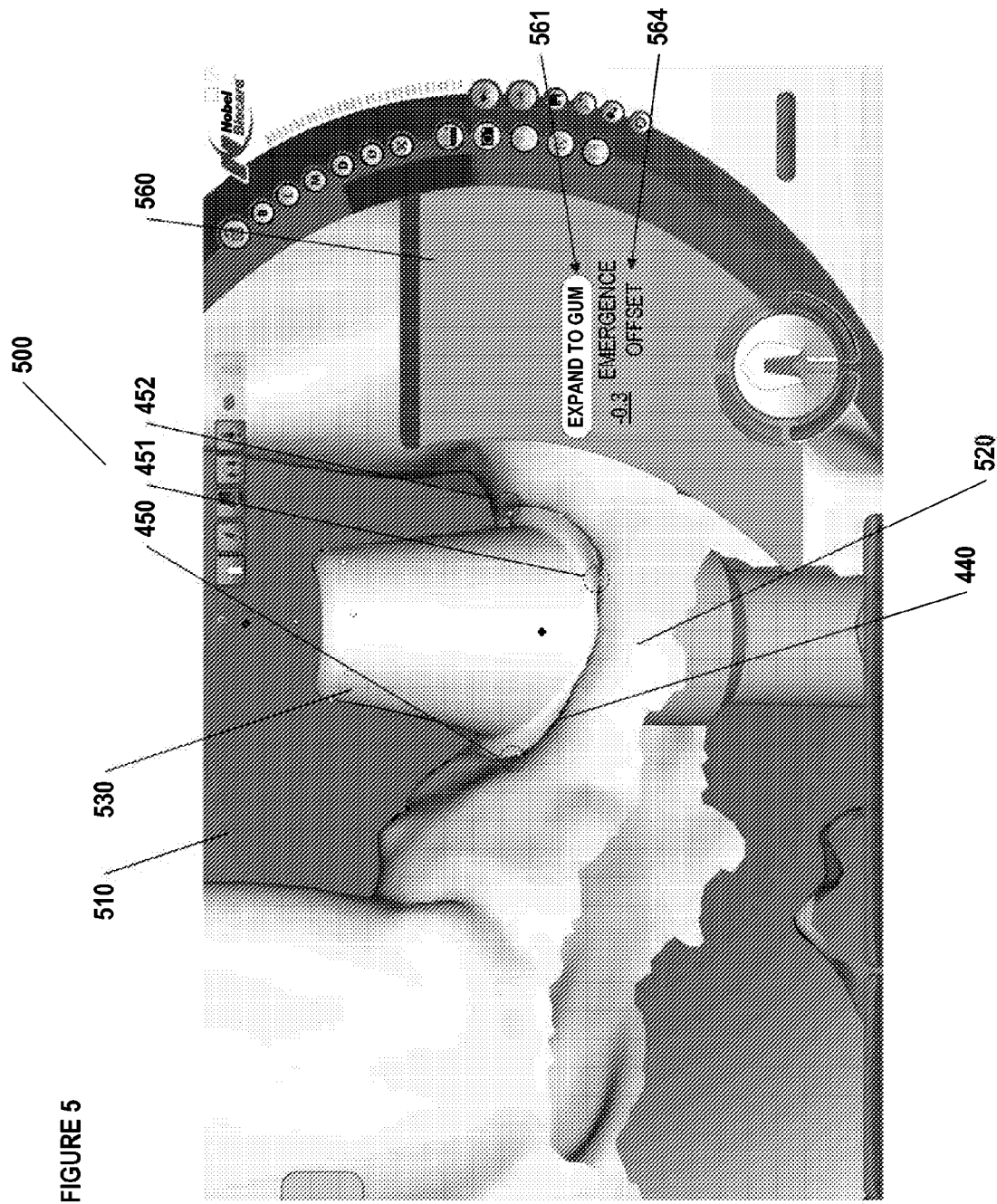
FIG. 5 illustrates a third interface for adjusting dental prostheses based on soft tissue.
Figure 6:
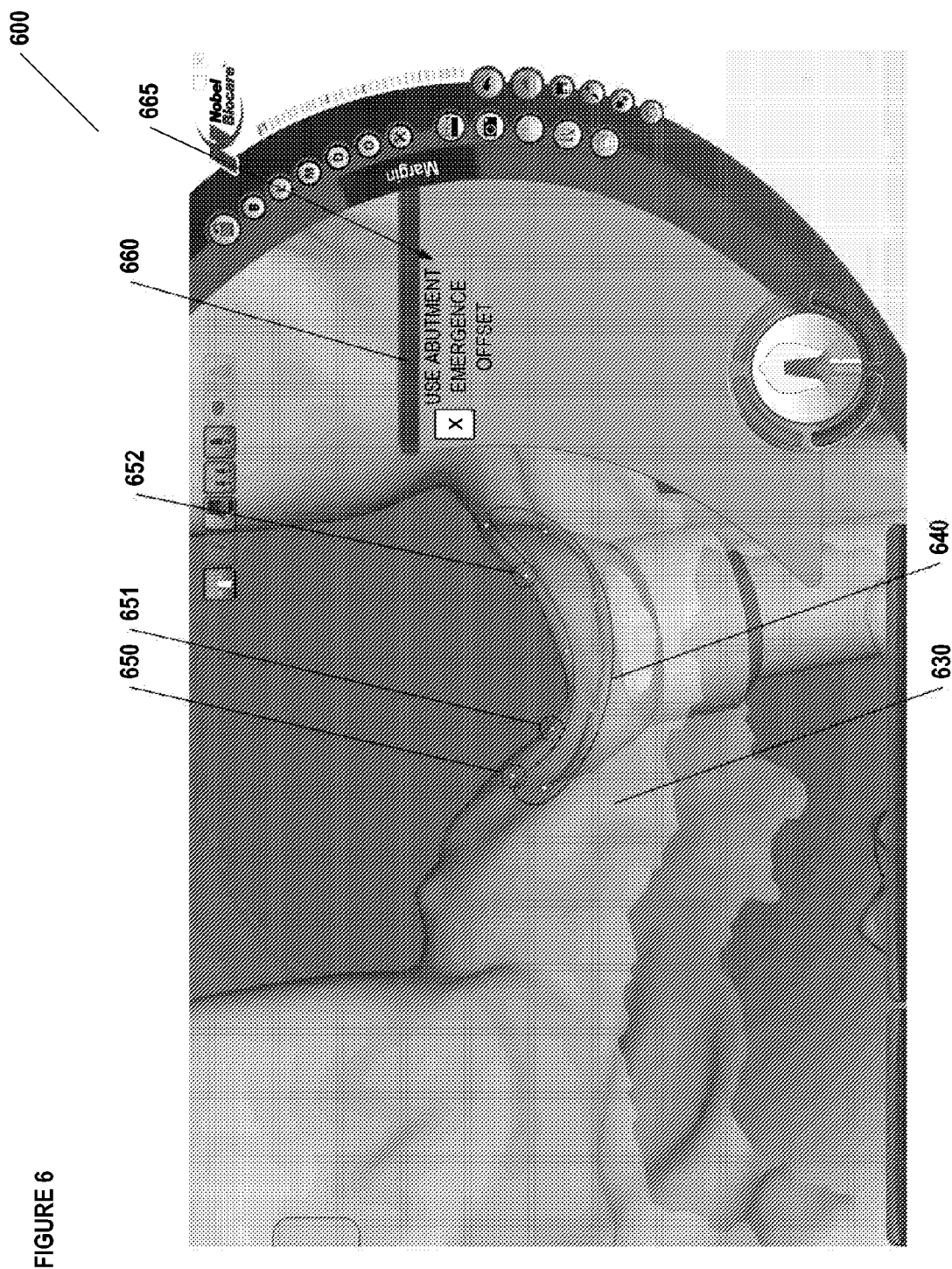
FIG. 6 illustrates a fourth interface for adjusting dental prostheses based on soft tissue.

FIG. 5 depicts an interface 500 with an overlaid representation portion 510 and a control menu 560. In some embodiments, the operator can define an emergence offset using an offset indicator 564 on control menu 560. After the emergence offset 564 is defined, the operator can press button 561 to adjust the dental prosthesis to the soft tissue, offset by the emergence offset. This dental prosthesis is depicted as 530 in FIG. 5. Adjustments made to the surface of the 3D model of the prosthesis based on the emergence offset can be in any direction. For example, in some embodiments, the adjustments are made in a radial direction extending from the axis of the prosthesis outward.

The emergence offset can define how the "emergence surface" of the 3D model of the dental prosthesis is positioned with respect to the emergence portion of the 3D scan of the soft tissue. In various embodiments, the emergence surface may be the portion of the dental prosthesis' surface that extends from the implant, through the soft tissue, and ends where the dental prosthesis emerges from the soft tissue—at the emergence limit (e.g., emergence limit 440 of FIGS. 4 and 5). The phrase "emergence surface of the 3D model of the dental prosthesis" has its ordinary and customary meaning, which includes a surface on the 3D model of the dental prosthesis that roughly corresponds to the emergence portion of the 3D scan of the soft tissue. For example, in some embodiments, the emergence surface of the 3D model of the dental prosthesis may extend from the interface of the 3D model of the prosthesis with the underlying implant, up to an emergence limit. For example, see FIG. 10, which depicts an emergence surface 1080 of 3D model of the dental prosthesis 1030 being depicted on the overlaid representation portion 1010 of interface 1000.

In some embodiments, the operator can define positive or negative emergence offsets. A positive offset indicates that the 3D model of the dental prosthesis will not extend as far, in a radial direction, for example, as the 3D scan of the gum. In particular, the emergence surface of the 3D model of the dental prosthesis will not cross over or extend beyond the emergence portion of the 3D scan of the soft tissue. On the other hand, if the offset is negative, then the emergence surface of the 3D model of the dental prosthesis may extend beyond, in the radial direction, for example, and be wider or have a greater circumference than the emergence portion of the 3D scan of the soft tissue of the patient. In this way, the operator can very quickly and easily define an emergence surface of a 3D model of a prosthesis, such as an abutment, with the desired gap or compression of soft tissue. In some embodiments, the effect of the signs of the offsets may be swapped, with negative offsets being associated with a gap and positive offsets being associated with the emergence surface of the dental prosthesis being wider than the scan of the soft tissue.

Example Systems for Adjusting Prostheses Based on Soft Tissue

Figure 2:
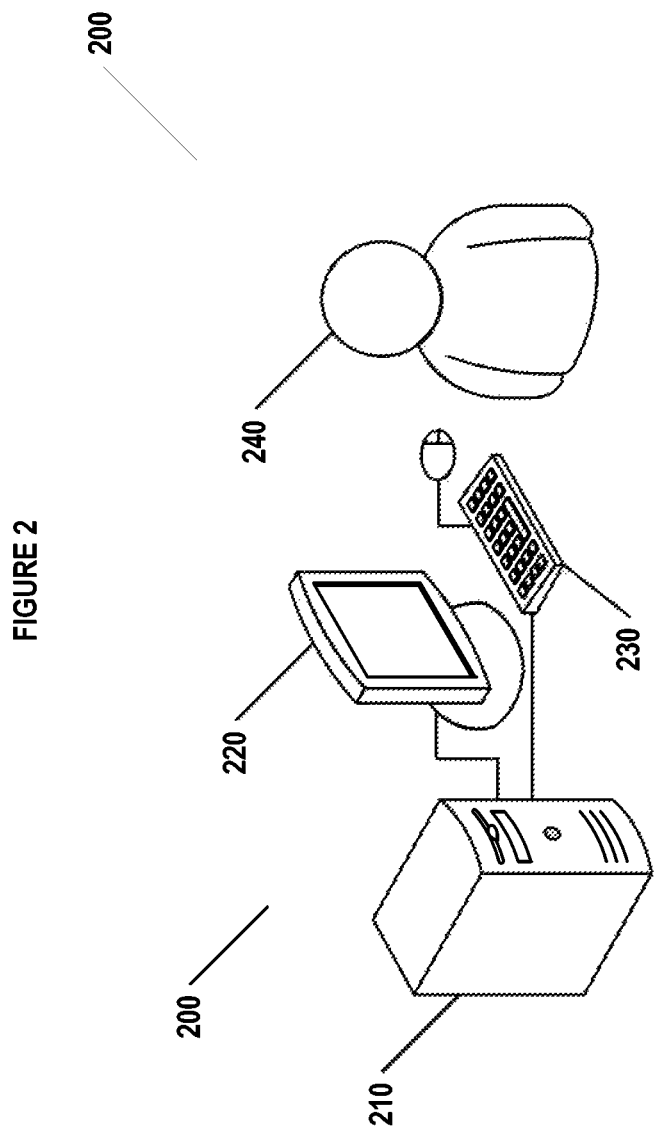
FIG. 2 illustrates an example system for adjusting dental prostheses based on soft tissue.

FIG. 2 illustrates an example system 200 for adjusting prostheses based on soft tissue. The system 200 may include one or more computers 210 coupled to one or more displays 220, and one or more input devices 230. An operator 240, who may be a dentist, dental technician, or other person, may plan dental prostheses using system 200 by manipulating the one or more input devices 230, such as a keyboard and/or a mouse. In some embodiments, while working on the dental plan, the operator 240 may view the dental plan and other related dental plan data on the display 220. The display 220 may include two or more display regions or portions, each of which displays a different view of the dental plan. For example, in some embodiments, the display 220 may show a semi-realistic 3D rendering of the dental plan, a localized abstraction of the dental plan, and/or a cross-sectional representation of the dental plan. Each of these displays or portions may be linked internally within a program and/or using data on computer 210. For example, a program running on a computer 210 may have a single internal representation of the dental plan in memory and the internal representation may be displayed in two or more abstract or semi-realistic manners on display 220.

In some embodiments, the operator 240 may be able to perform a command, such as select, move, manipulate, or make transparent, opaque, or invisible, on a particular substructure in the dental plan. The operator 240 may be able to perform this command by manipulating the input device 230, such as clicking with a mouse on a particular region of one of the abstract or semi-realistic versions of the dental plan displayed on the display 220.

In various embodiments, the computer 210 may include one or more processors, one or more memories, and one or more communication mechanisms. In some embodiments, more than one computer may be used to execute the modules, methods, blocks, and processes discussed herein. Additionally, the modules and processes herein may each run on one or multiple processors, on one or more computers; or the modules herein may run on dedicated hardware. The input devices 230 may include one or more keyboards (one-handed or two-handed), mice, touch screens, voice commands and associated hardware, gesture recognition, or any other means of providing communication between the operator 240 and the computer 210. The display 220 may be a two-dimensional ("2D") or 3D display and may be based on any technology, such as LCD, CRT, plasma, projection, etc.

The communication among the various components of system 200 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 200 may also be combined into a single unit or module. In some embodiments, all of the electronic components of system 200 are included in a single physical unit or module.

Techniques for Adjusting Prostheses Based on Soft Tissue

Figure 3:
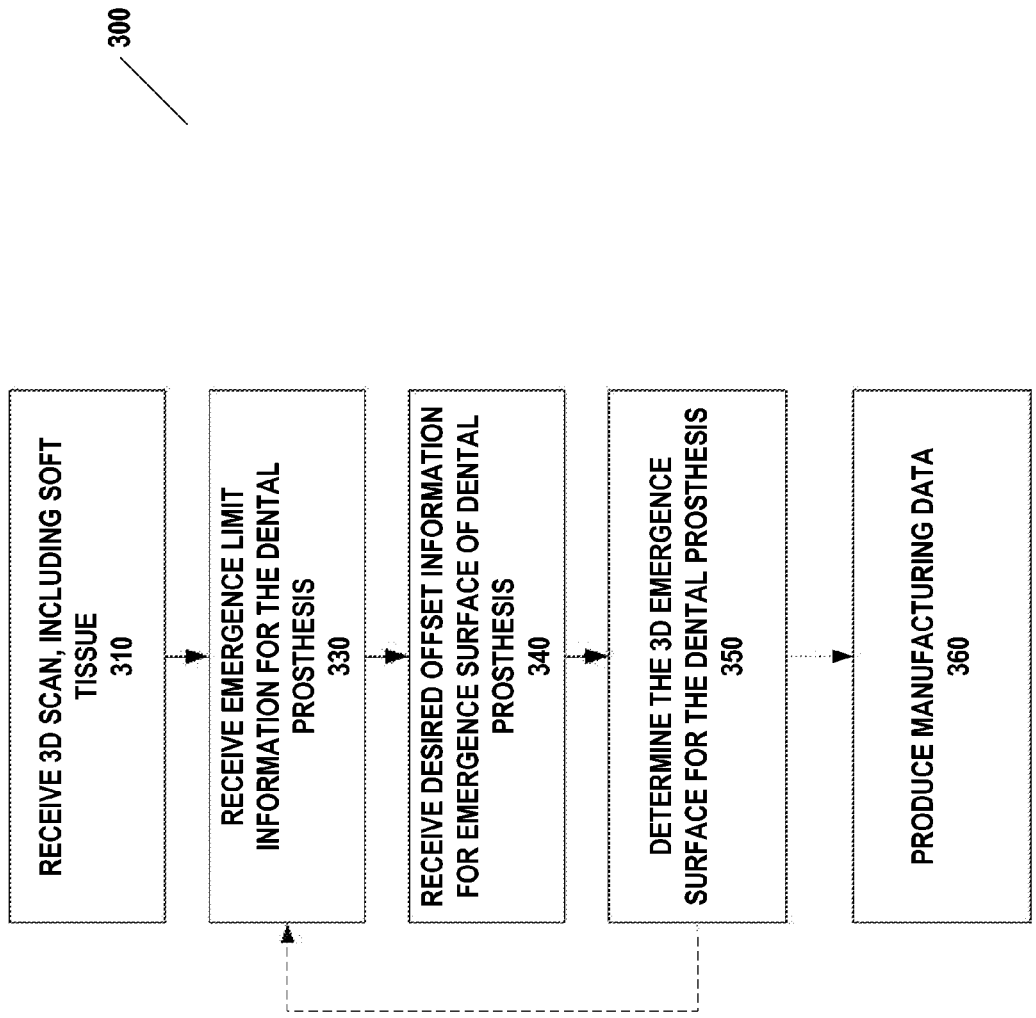
FIG. 3 illustrate an example method of adjusting dental prostheses based on soft tissue.

FIG. 3 depicts a method 300 for adjusting a dental prosthesis based on soft tissue. In block 310, a 3D scan of soft tissue is received. As discussed above, this 3D scan may contain an emergence portion that defines the area in which a dental prosthesis, such as an abutment, will be proximal to the soft tissue. For example, if a dental surgeon implanted an implant into a patient and then placed a healing abutment into the implant, soft tissue would form through an emergence portion down to the implant. Thereafter, the healing abutment would be taken out and a scan of the soft tissue would take place. That scan would be received in block 310. An example of that scan is depicted as 3D model 120 in FIG. 1. The scan may be taken using any appropriate method including an intraoral scan, CT scan, MRI's, and the like. The scan could also be, in some embodiments, a surface scan of a physical model, where, for example, there is an implant replica representing the position of the implant relative to the soft tissue. The scan may be of the physical model, but it nevertheless can represent the 3D surface of the soft tissue. Various embodiments of scanning 3D models are given in U.S. patent application Ser. No. 12/703,596, entitled "Dental Data Planning," filed Feb. 10, 2010, incorporated herein by reference in its entirety for all purposes.

In block 310, placement information for a dental prosthesis may also be received. For example, some embodiments detect the position of the implant (e.g., by using an implant locator in a scan of a model). The position of the prosthesis or other abutment can be determined from the position of the implant. In some embodiments, a position locator could be attached to a model, and the model with the position locator attached could be scanned. The position of the implant can be defined from the position of the position locator in the scan. When a 3D model of a prosthesis is "attached" to the implant in the design software, the position of the prosthesis is thereby defined. The placement information may be, looking to the Example in FIG. 1, that an abutment 130 will be placed on top of an implant through the 3D scan of the soft tissue 120, thereby obtaining the position of the abutment 120 in part, and indirectly, from the position of the implant.

In block 330, emergence limit information for a dental prosthesis is received. The emergence limit information may be a margin line or other line or curve defining the upper limit of the emergence surface of the 3D model of the dental prosthesis. For example, looking to FIG. 4, defining the emergence limit 440 may be defined by manipulating manipulators 450, 451, 452. As noted elsewhere herein, the emergence limit 440 and the base of the 3D model of the prosthesis (e.g., a fixed diameter interface with the implant to which the 3D model of the prosthesis is attached) together may define the emergence surface of the 3D model of the dental prosthesis. In some embodiments, the manipulators 450-452 are used to define the emergence limit 440. In some embodiments, the manipulators 450-452 for an emergence limit 440 may be sorted radially (e.g., about the center axis of the associated implant)—and the emergence limit 440 may be determined based on the sorted manipulators 450-452. The emergence limit 440 may be defined as a curved line that passes through the manipulators 450-452. The emergence limit 440 may be formed using any appropriate algorithm or interpolation among these manipulators 450-452, including a second-degree NURBS curve, a spline, other NURBS, etc. In various embodiments, the operator can add manipulation points to an emergence limit 440 by clicking on the line 440, clicking on the 3D surface 420, and the like. The addition of manipulators may allow the operator to refine the emergence limit 440. In various embodiments, the operator can also remove manipulation points 450-452 from the emergence limit 440 by dragging manipulators 450-452 off the screen, right-clicking on manipulators 450-452, performing particular keystrokes, and the like.

Figure 11:
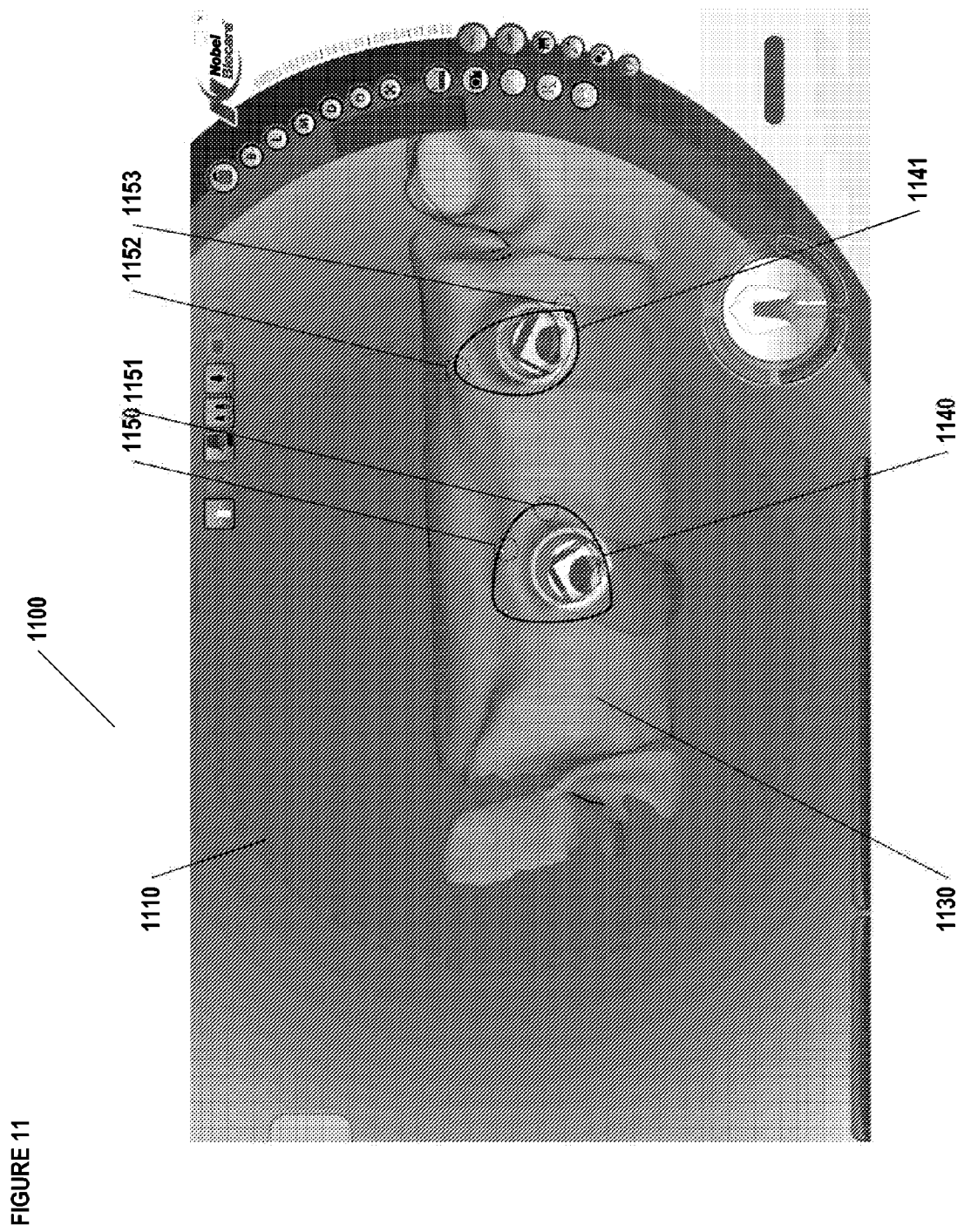
FIG. 11 illustrates a ninth interface for adjusting dental prostheses based on soft tissue.

FIG. 11 illustrates an interface 1100 with an overlapped representation portion 1110 depicting two emergence limits 1140 and 1141 on the 3D scan of soft tissue 1130. When there is more than one implant and more than one emergence limit 1140, 1141, the techniques herein may sort any received or defined manipulators 1150, 1151, 1152, 1153 by their proximity to implants and thereby define which of the manipulators 1150, 1151, 1152, 1153 are associated with each emergence limit 1140, 1141 (e.g., by associating manipulators 1150-1153 with the implant to which it is closest). From there, the manipulators 1150, 1151 that are associated together are used to define the emergence limit 1140, as described above. As described above, manipulators may be added to an emergence limit. For example, looking at emergence limit 1141, we see that it crosses over an "open space" as it interpolates between two of the manipulators 1152 and 1153. An operator may want to add another manipulator in order to match the emergence limit 1141 to the surface 1130 and/or to alter the emergence limit's 1141 shape.

After the emergence limit information for the dental prosthesis is received in block 330, then desired offset information for the emergence surface of the 3D model of the dental prosthesis is received in block 340. As discussed above and as depicted in FIG. 5, the emergence limit information may be received from an operator using the emergence offset interface 564 on control menu 560. The operator may be able to type in the emergence offset or a scroll bar, dial, or other input may be used. In some embodiments, as depicted in FIG. 5, once the operator is satisfied with the placement of the emergence limit, as defined by manipulators 450, 451, 452, the operator may press a button or otherwise cause to be executed the determination of the emergence surface for the 3D model of the dental prosthesis, such as by pressing button 561 on control menu 560. In other embodiments, as the emergence offset is changed and/or the emergence limit is changed, the techniques herein may automatically update the emergence surface for the 3D model of the dental prosthesis.

Figure 9:
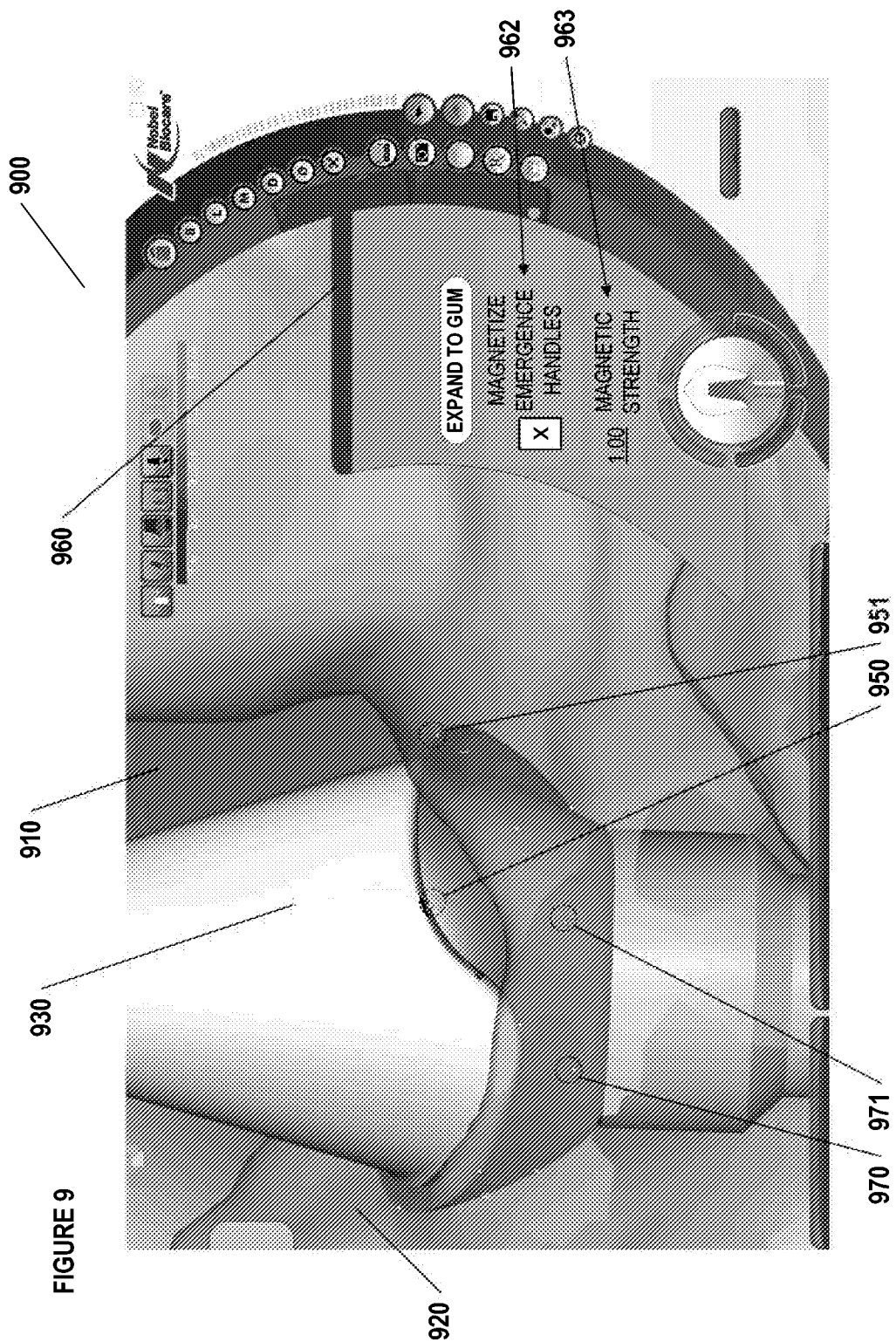
FIG. 9 illustrates a seventh interface for adjusting dental prostheses based on soft tissue.
Figure 12:
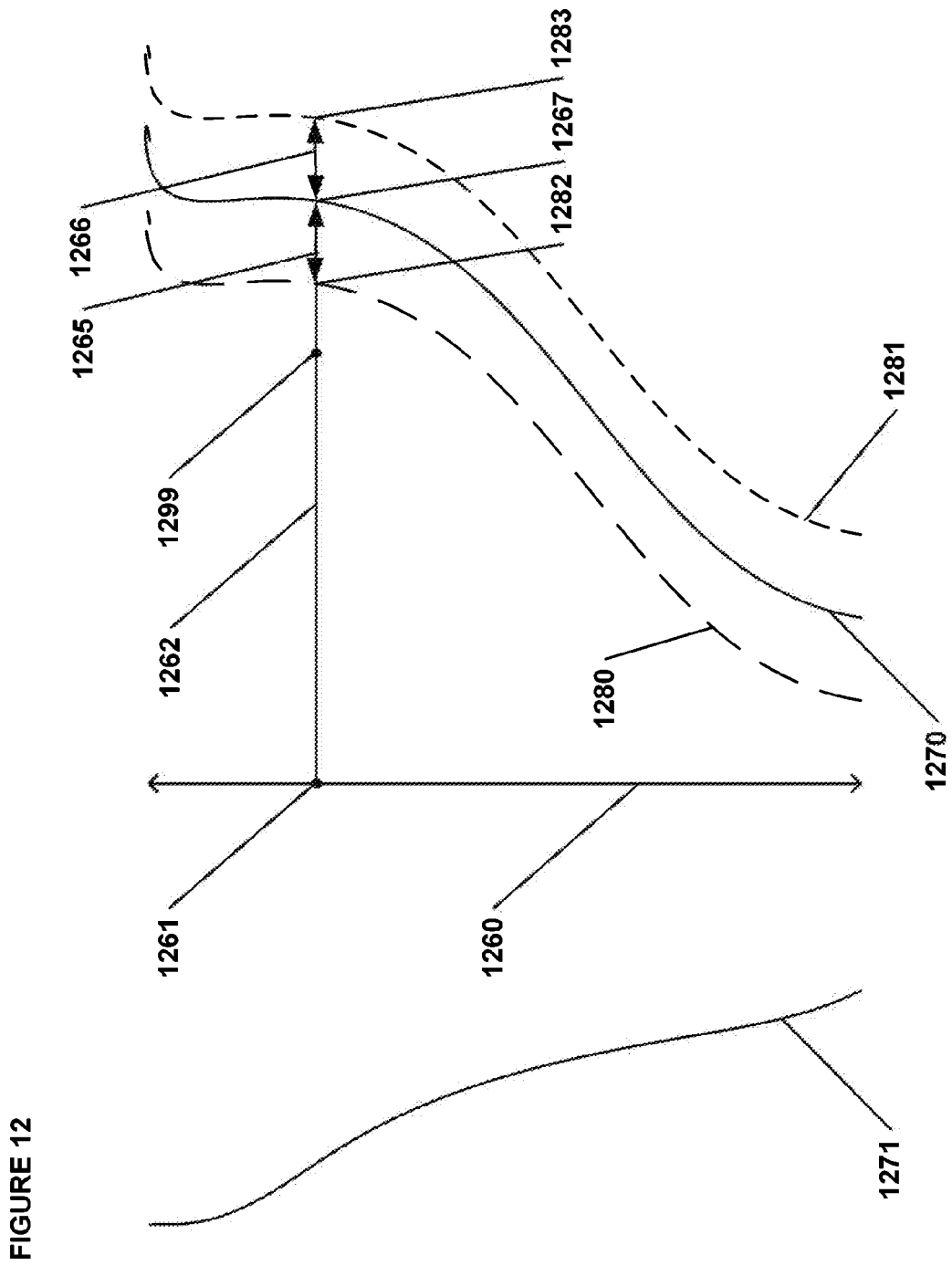
FIG. 12 illustrates an example schematic for adjusting dental prostheses based on soft tissue.

Determining the 3D surface for the emergence surface of the 3D model of the dental prosthesis in block 350 may include determining a surface based on the offset and based on the emergence portion of the 3D scan of the soft tissue. For example, FIG. 12 depicts a cross-section of an emergence portion of a 3D scan of soft tissue with the two sides 1270 and 1271. The dental prosthesis for which the emergence surface will be defined has an axis 1260. The axis may be associated with the central axis of an implant, the central axis of the prosthesis, an insertion axis, and the like. For example, if the axis 1260 is associated with an implant axis, then the axis can be defined based on a scan of a physical implant position locator either, e.g., on the physical model or in a physical impression taken of a patient's mouth. In some embodiments, determining the emergence surface comprises determining, for each manipulator 1299 on the emergence surface of the 3D model of the dental prosthesis (not depicted in FIG. 12), the point 1261 along a perpendicular line 1262 from the manipulator 1299 to the axis 1260. From there, the point 1267 is determined as the point where the perpendicular line 1262 intersects the 3D soft tissue surface 1270. The corresponding point 1282 for the emergence surface 1280 is defined as the point 1282 on the perpendicular line 1262 that is offset by the desired offset 1265. As is illustrated in the FIG. 12, the desired offset can be positive (e.g., distance 1265) and define a point 1282, or negative (distance 1266) and define a point 1283. This process is repeated for each manipulator 1299 on the emergence surface of the 3D model of the dental prosthesis. As discussed in more detail below with respect to FIG. 9, the manipulators may be on the emergence limit line (manipulators 950 and 951) as well as on other parts of the emergence surface (manipulators 970 and 971). Embodiments herein include offsetting each of these manipulators 950, 951, 970, and 971. In some embodiments, this process of offsetting points is repeated for only the manipulators. In other embodiments, the process of offsetting points is repeated for more points than just the manipulators—for example, an entire grid of points may be offset.

Once all of the manipulators 1299 and other points have been offset relative to the emergence portion of the 3D scan of the soft tissue, the emergence surface of the 3D model of the dental prosthesis can then be defined as a second degree NURBS surface through the manipulation points (and any other points that have been offset from the 3D surface of the soft tissue), or may be interpolated or estimated in any appropriate way. There are other methods of calculating the emergence surface for the 3D model of the dental prosthesis, and these are considered within the scope of the embodiments herein. For example, the emergence surface of the 3D model of the dental prosthesis may be determined by radially scaling the emergence portion of the 3D scan of the soft tissue in order to offset the emergence surface of the 3D model of the dental prosthesis by the appropriate amount, as defined by the offset.

Figure 7:
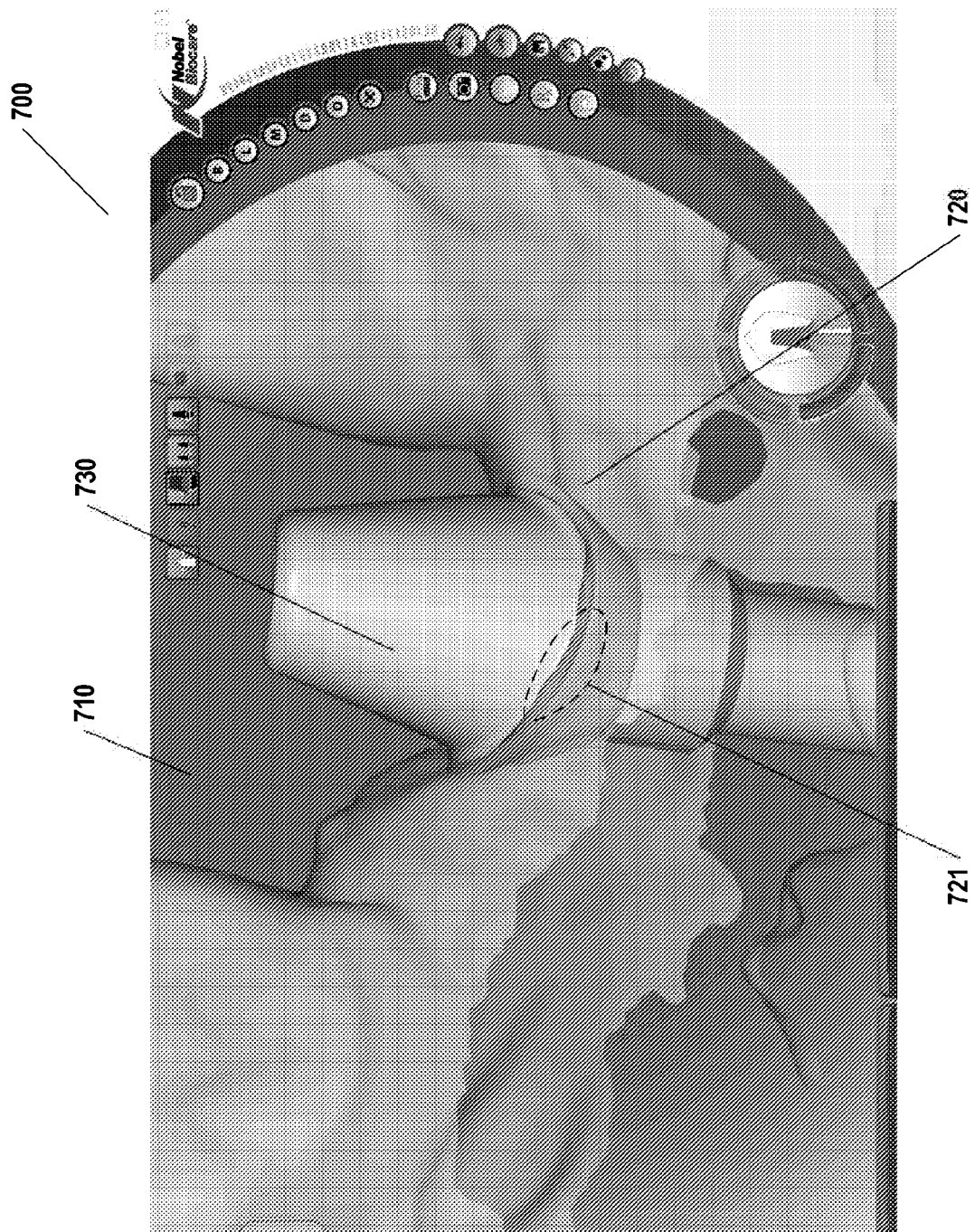
FIG. 7 illustrates a fifth interface for adjusting dental prostheses based on soft tissue.
Figure 8:
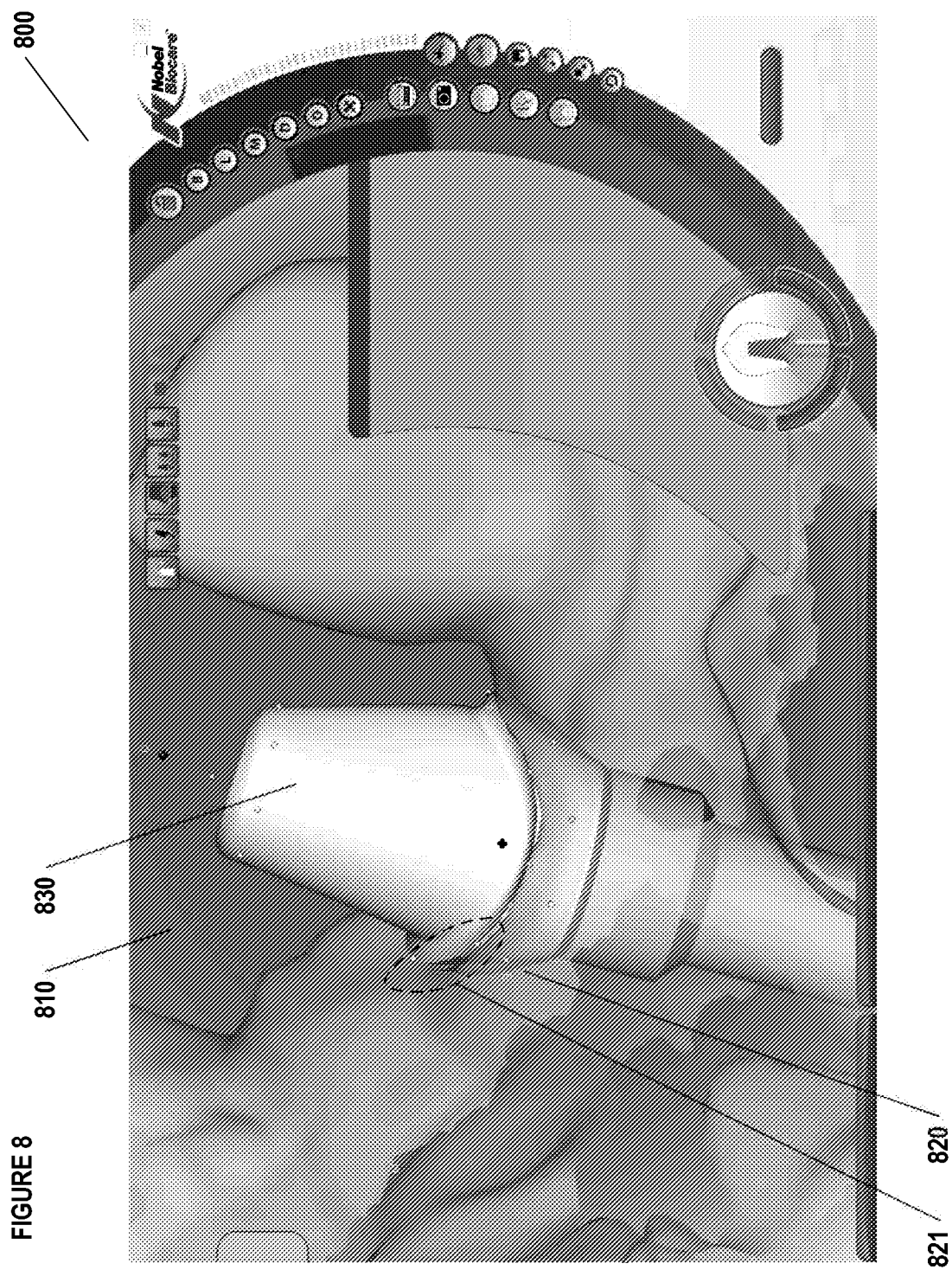
FIG. 8 illustrates a sixth interface for adjusting dental prostheses based on soft tissue.

After the emergence surface of the 3D model of the dental prosthesis has been generated in block 350, the operator may see the generated dental prosthesis on the overlaid representation portion of the interface. For example, turning to FIG. 7, the operator will be able to see on interface 700 the overlaid representation portion 710 which will include a dental prosthesis 730 and a 3D scan of soft tissue 720. As depicted in FIG. 7, if the offset causes the dental prosthesis model to be larger than the 3D scan of the soft tissue in its emergence portion, then the dental prosthesis' emergence surface will overlap with the 3D scan, as signaled with area 721. On the other hand, if the emergence offset is such that the dental prosthesis is smaller than the related emergence portion of the 3D scan of the soft tissue, then a gap 821, shown in FIG. 8, may be seen between the 3D scan of the soft tissue 820 and the prosthesis 830.

After the 3D surface for the emergence surface of the 3D model of the dental prosthesis has been determined in block 350, the operator may optionally manipulate the limit information (in block 330, discussed above) and offset information (in block 340, discussed above) again. From there, a new 3D surface for the emergence surface of the 3D model of the dental prosthesis may be determined in block 350. Once the operator is satisfied with the prosthesis or is ready to produce the prosthesis, the operator may continue to other steps in prosthesis design (not depicted in FIG. 3) or may produce manufacturing data for the prosthesis (block 360).

Magnetization

There are numerous other embodiments of the techniques, systems, methods, computer-readable storage media, and methods discussed herein. For example, different steps may be added to method 300 and/or steps in method 300 may be performed in a different order or not at all. For example, turning to FIG. 9, in some embodiments, the operator may be able to manipulate the manipulators 950, 951, 970, and/or 971 in order to further modify the emergence surface of the 3D model of the dental prosthesis (not depicted in the method 300 of FIG. 3). Further, in some embodiments, the operator may be able to select an option 962 on control menu 960 to magnetize the emergence handles of the dental prosthesis. By doing this, the operator may be able to change the emergence surface while still maintaining the desired offset between the emergence surface of the 3D model of the dental prosthesis and the 3D scan of the soft tissue. In some embodiments, the "magnetization" will be in effect for all movements of manipulators 950, 951, 970, and/or 971 that are within a predetermined distance from the 3D scan of the soft tissue. The distance may be predefined or may be defined by the user using a magnetization distance control 963 on control menu 960. If a manipulator 950, 951, 970, or 971 is moved beyond this threshold magnetization distance, then the manipulator will move freely and the emergence surface will be manipulated freely and will not be confined to the offset with the 3D scan of the soft tissue, otherwise the manipulator will be held to the desired offset with the 3D scan of the soft tissue.

Magnetization may operate using any appropriate technique or algorithm. For example, the operator may move a manipulator 970 by clicking on the point and holding down a mouse button until she has placed it where she likes. If that point is still within the magnetization distance of the 3D scan of the soft tissue 920, then, once released, the closest point on the 3D surface of the soft tissue 920 will be found and the manipulator 970 will be placed at the desired offset from the point closest point on the 3D surface of the soft tissue 920. If the point is not within the magnetization distance of the 3D scan of the soft tissue 920, then it placement may not be changed after placement by the user.

Coloring

Figure 10:
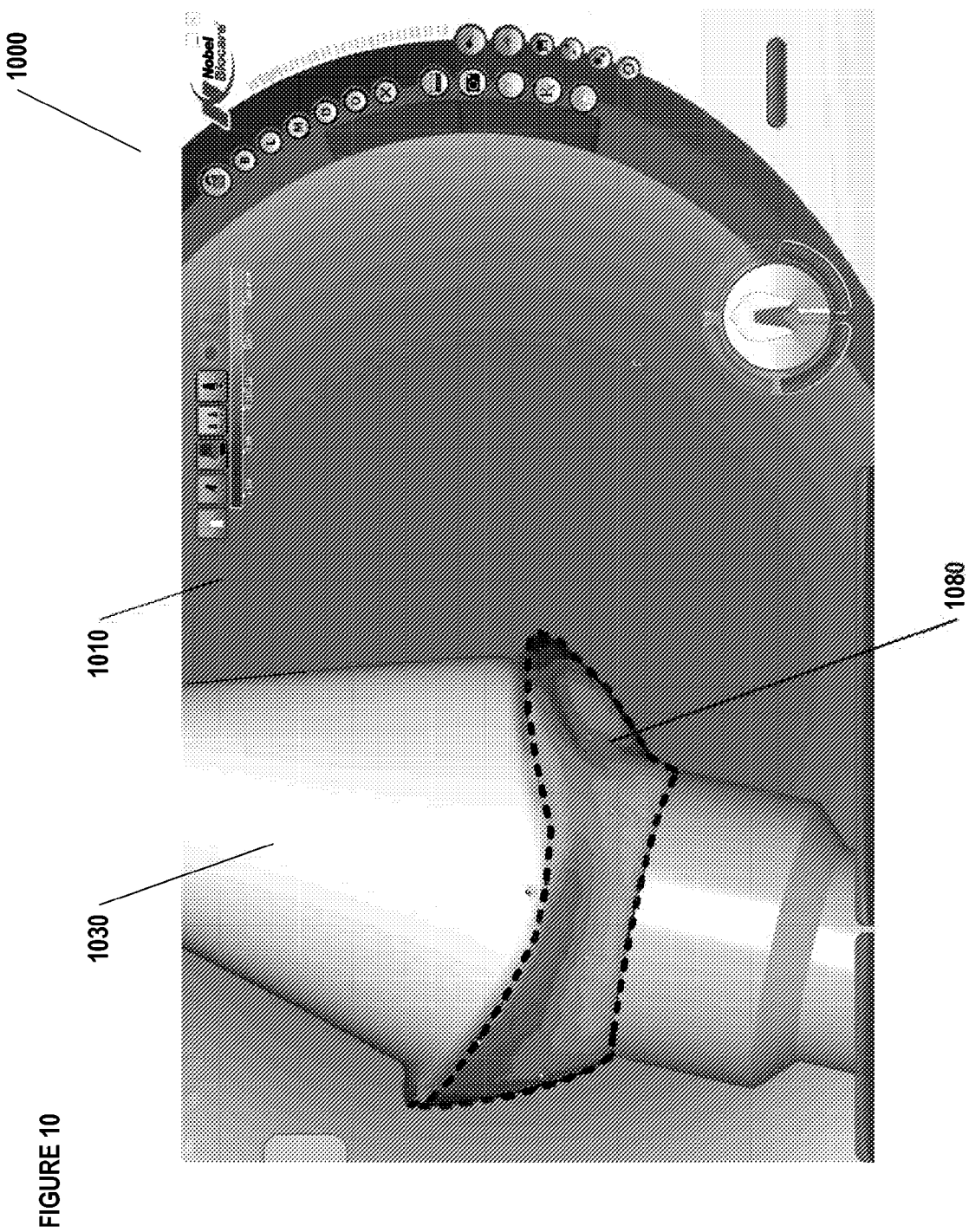
FIG. 10 illustrates an eighth interface for adjusting dental prostheses based on soft tissue.

Turning now to FIG. 10, in various embodiments the emergence surface of the 3D model of the dental prosthesis may be colored or shaded in order to show the distance between the emergence surface of the 3D model of the dental prosthesis and the emergence portion of the 3D scan of the soft tissue. For example, the emergence surface of the 3D model of the dental prosthesis may be covered with a color map, and the color map may have different colors or color ranges that represent different distances between the emergence surface of the 3D model of the prosthesis and the emergence portion of the 3D scan of the soft tissue. Example coloring is depicted in FIG. 10 in the interface 1000, which has an overlaid representation portion 1010 that shows a dental prosthesis 1030 that has a shaded emergence surface 1080. In some embodiments and in some procedures, the operator may want to keep the distance between the soft tissue, such as the gingiva or gum, within a certain distance (e.g., 0.1 mm or 1 mm) of the emergence surface in order to avoid a gap larger than that size or to compress the soft tissue more than that amount. Coloring or shading on the emergence surface of the 3D model of the dental prosthesis can help an operator quickly identify the areas of the surface that are inside and outside of a desired range.

Other Embodiments

Various of the embodiments herein show interfaces of a certain configuration. Other configurations of interfaces are also possible. Turning to FIG. 13, it is possible that an interface 1300 can have an overlaid representation portion 1310, a global selection portion 1311, and a control menu 1360, all on a single interface 1300. It is also possible, as depicted in FIG. 14, that two separate sub-interfaces 1400 and 1401 may be used. The control menu 1460 may be on interface portion 1401 and the overlaid representation portion 1410 and global selection portion 1411 may be on interface portion 1400. These various interface portions may be shown on separate screens, on separate displays or in separate windows. Other configurations of the various portions on various displays or in various windows may also be used.

The processes and systems described herein may be performed on or encompass various types of hardware, such as computing devices. In some embodiments, computer 210, display 220, and/or input device 230 may each be separate computing devices, applications, or processes or may run as part of the same computing devices, applications, or processes—or one of more may be combined to run as part of one application or process—and/or each or one or more may be part of or run on computing devices. Computing devices may include a bus or other communication mechanism for communicating information, and a processor coupled with the bus for processing information. The computing devices may have a main memory, such as a random access memory or other dynamic storage device, coupled to the bus. The main memory may be used to store instructions and temporary variables. The computing devices may also include a read-only memory or other static storage device coupled to the bus for storing static information and instructions. The computer systems may also be coupled to a display, such as a CRT or LCD monitor. Input devices may also be coupled to the computing devices. These input devices may include a mouse, a trackball, or cursor direction keys.

Each computing device may be implemented using one or more physical computers, processors, embedded devices, or computer systems or a combination or portions thereof The instructions executed by the computing device may also be read in from a computer-readable medium. The computer-readable medium may be a CD, DVD, optical or magnetic disk, laserdisc, carrier wave, or any other medium that is readable by the computing device. In some embodiments, hardwired circuitry may be used in place of or in combination with software instructions executed by the processor. Communication among modules, systems, devices, and elements may be over direct or switched connections, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

Any appropriate 3D graphics processing may be used for displaying or rendering, including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements, and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A computer-implemented method for adjusting dental prostheses based on soft tissue, comprising:
receiving a 3D scan of soft tissue of a patient, said 3D scan of the soft tissue of the patient comprising at least an emergence portion, said emergence portion of the 3D scan of the soft tissue extending from an area associated with an implant attached to said patient, to an area where a dental prosthesis attached to said implant would emerge from said soft tissue;
receiving emergence limit information for an emergence surface of a 3D model of the dental prosthesis;
receiving desired offset information for the emergence surface of the 3D model of the dental prosthesis, wherein the offset information comprises a distance between the emergence surface of the 3D model of the dental prosthesis and the emergence portion of the 3D scan of the soft tissue;

determining a shape of the emergence surface of the 3D model of the dental prosthesis based on the emergence portion of the 3D scan of the soft tissue, the emergence limit information, and the offset information, wherein said shape is automatically determined by one or more computing devices based on the emergence portion of the 3D scan of the soft tissue, the emergence limit information, and the offset information;

further modifying the emergence surface of the 3D model by manipulating manipulators of the 3D model of the dental prosthesis, wherein the manipulators are magnetized, such that an operator may change the emergence surface of the 3D model while still maintaining said distance between the emergence surface of the 3D model of the dental prosthesis and the 3D scan of the soft tissue, unless a manipulator of said manipulators is moved beyond a predetermined threshold monetization distance, in which case the manipulator moves freely and the emergence surface is manipulated freely; and producing manufacturing data related to the dental prosthesis.

2. The method of claim 1, wherein determining the emergence surface of the 3D model of the dental prosthesis comprises determining a 3D surface that is offset from the emergence portion of the 3D scan of the soft tissue by an offset associated with the desired offset information.

3. The method of claim 1, wherein determining the emergence surface of the 3D model of the dental prosthesis comprises determining a surface of the 3D model of the prosthesis from the area associated with the implant and to approximately an emergence limit associated with the emergence limit information.

4. The method of claim 1, wherein determining the emergence surface of the 3D model of the dental prosthesis comprises determining the emergence surface of the 3D model of an abutment.

5. The method of claim 1, wherein receiving desired offset information comprises receiving information to extend the emergence surface of the 3D model of the dental prosthesis beyond, in a radial direction, the emergence portion of the 3D scan of the soft tissue.

6. The method of claim 1, wherein receiving desired offset information comprises receiving information to provide a gap between the emergence surface of the 3D model of the dental prosthesis and the emergence portion of the 3D scan of the soft tissue.

7. The method of claim 1, wherein the method further comprises receiving placement information for the 3D model of the dental prosthesis relative to the 3D scan of the soft tissue.

8. The method of claim 1, wherein receiving the emergence limit information comprises receiving placement information for a margin line on the 3D surface of the soft tissue from an operator.

9. The method of claim 8, wherein determining the emergence surface of the 3D model of the dental prosthesis comprises determining a 3D surface for the dental prosthesis from the base of the prosthesis up to the margin line.

10. The method of claim 1, wherein receiving placement information for a dental prosthesis comprises receiving a central axis for the dental prosthesis; and wherein determining the emergence surface of the 3D model of the dental prosthesis comprises determining the emergence surface of the 3D model of the dental prosthesis based at least in part on the central axis for the dental prosthesis.

11. A system for adjusting dental prostheses based on soft tissue, comprising one or more computing devices, said one or more computing devices being configured to:

receive a 3D scan of soft tissue of the a patient, said 3D scan of the soft tissue of the patient comprising at least an emergence portion, said emergence portion of the 3D scan of the soft tissue extending from an area associated with an implant attached to said patient, to an area where a dental prosthesis attached to said implant would emerge from said soft tissue;

receive emergence limit information for an emergence surface of a 3D model of the dental prosthesis;

receive desired offset information for the emergence surface of the 3D model of the dental prosthesis, wherein the offset information comprises a distance between the emergence surface of the 3D model of the dental prosthesis and the emergence portion of the 3D scan of the soft tissue;

automatically determine a shape of the emergence surface of the 3D model of the dental prosthesis based on the emergence portion of the 3D scan of the soft tissue, the emergence limit information, and the offset information;

wherein the emergence surface of the 3D model is further modified by manipulating manipulators of the 3D model of the dental prosthesis, wherein the manipulators are magnetized, such that an operator may change the emergence surface of the 3D model while still maintaining said distance between the emergence surface of the 3D model of the dental prosthesis and the 3D scan of the soft tissue, unless a manipulator of said manipulators is moved beyond a predetermined threshold magnetization distance, in which case the manipulator moves freely and the emergence surface is manipulated freely; and produce manufacturing data related to the dental prosthesis.

12. The system of claim 11, wherein determining the emergence surface of the 3D model of the dental prosthesis comprises determining a 3D surface that is offset from the emergence portion of the 3D scan of the soft tissue by an offset associated with the desired offset information.

13. The system of claim 11, wherein determining the emergence surface of the 3D model of the dental prosthesis comprises determining a surface of the 3D model of the prosthesis from the area associated with the implant and to approximately an emergence limit associated with the emergence limit information.

14. The system of claim 11, wherein receiving desired offset information comprises receiving information to extend the emergence surface of the 3D model of the dental prosthesis beyond, in a radial direction, the emergence portion of the 3D scan of the soft tissue.

15. The system of claim 11, wherein receiving desired offset information comprises receiving information to provide a gap between the emergence surface of the 3D model of the dental prosthesis and the emergence portion of the 3D scan of the soft tissue.

16. A non-transitory computer-readable storage medium having embodied thereon in a non-transitory manner computer-executable instructions for adjusting dental prostheses based on soft tissue, said computer-executable instructions, when running on one or more computing devices, performing a method comprising:

receiving a 3D scan of soft tissue of the a patient, said 3D scan of the soft tissue of the patient comprising at least an emergence portion, said emergence portion of the 3D scan of the soft tissue extending from an area associated with an implant attached to said patient, to an area where a dental prosthesis attached to said implant would emerge from said soft tissue;

receiving emergence limit information for an emergence surface of a 3D model of the dental prosthesis;

receiving desired offset information for the emergence surface of the 3D model of the dental prosthesis, wherein the offset information comprises a distance between the emergence surface of the 3D model of the dental prosthesis and the emergence portion of the 3D scan of the soft tissue;

automatically determining, using one or more computing devices, a shape of the emergence surface of the 3D model of the dental prosthesis based on the emergence portion of the 3D scan of the soft tissue, the emergence limit information, and the offset information;

further modifying emergence surface of the 3D model by manipulating manipulators of the 3D model of the dental prosthesis, wherein the manipulators are magnetized, such that an operator may change the emergence surface of the 3D model while still maintaining said distance between the emergence surface of the 3D model of the dental prosthesis and the 3D scan of the soft tissue, unless a manipulator of said manipulators is moved beyond a predetermined threshold monetization distance, in which case the manipulator moves freely and the emergence surface is manipulated freely; and producing manufacturing data related to the dental prosthesis.

17. The non-transitory computer-readable storage medium of claim 16, wherein determining the emergence surface of the 3D model of the dental prosthesis comprises determining a 3D surface that is offset from the emergence portion of the 3D scan of the soft tissue by an offset associated with the desired offset information.

18. The non-transitory computer-readable storage medium of claim 16, wherein determining the emergence surface of the 3D model of the dental prosthesis comprises determining a surface of the 3D model of the prosthesis from the area associated with the implant and to approximately an emergence limit associated with the emergence limit information.

19. The non-transitory computer-readable storage medium of claim 16, wherein receiving desired offset information comprises receiving information to extend the emergence surface of the 3D model of the dental prosthesis beyond, in a radial direction, the emergence portion of the 3D scan of the soft tissue.

20. The non-transitory computer-readable storage medium of claim 16, wherein receiving desired offset information comprises receiving information to provide a gap between the emergence surface of the 3D model of the dental prosthesis and the emergence portion of the 3D scan of the soft tissue.

* * * * *

UNITED STATES PATENT AND TRADEMARK OFFICE
CERTIFICATE OF CORRECTION

| | |
|---|---|
| PATENT NO. | : 8,712,733 B2 |
| APPLICATION NO. | : 12/885027 |
| DATED | : April 29, 2014 |
| INVENTOR(S) | : Jean-Sebastien Auclair Beaudry et al. |

It is certified that error appears in the above-identified patent and that said Letters Patent is hereby corrected as shown below:

In the Claims

Column 11, line 21, Claim 1, change "monetization" to --magnetization--.

Column 12, line 6, Claim 11, change "the a" to --a--.

Column 12, line 65, Claim 16, change "the a" to --a--.

Column 13, line 25, Claim 16, change "monetization" to --magnetization--.

Signed and Sealed this
Seventh Day of October, 2014

Michelle K. Lee
*Deputy Director of the United States Patent and Trademark Office*